United States Patent
Mr et al.

(10) Patent No.: US 12,208,188 B2
(45) Date of Patent: *Jan. 28, 2025

(54) AUTOMATIC RECHARGER BRINE PREPARATION FROM A SALT CARTRIDGE

(71) Applicant: MOZARC MEDICAL US LLC, Minneapolis, MN (US)

(72) Inventors: Kirankumar Mr, Bangalore (IN); Muhammed Mashal P K, Bangalore (IN)

(73) Assignee: MOZARC MEDICAL US LLC, Minneapolis, MN (US)

( * ) Notice: Subject to any disclaimer, the term of this patent is extended or adjusted under 35 U.S.C. 154(b) by 600 days.

This patent is subject to a terminal disclaimer.

(21) Appl. No.: 17/152,377

(22) Filed: Jan. 19, 2021

(65) Prior Publication Data

US 2022/0226552 A1 Jul. 21, 2022

(51) Int. Cl.
*A61M 1/16* (2006.01)
*B01J 20/04* (2006.01)
*B01J 20/34* (2006.01)

(52) U.S. Cl.
CPC ........ *A61M 1/1696* (2013.01); *A61M 1/1654* (2013.01); *B01J 20/048* (2013.01); *B01J 20/3475* (2013.01); *A61M 2205/3337* (2013.01); *B01J 2220/62* (2013.01)

(58) Field of Classification Search
CPC .............. A61M 1/1654; A61M 1/1696; A61M 2205/3337; B01J 20/048; B01J 20/3475; B01J 2220/62
See application file for complete search history.

(56) References Cited

U.S. PATENT DOCUMENTS

| | | | | |
|---|---|---|---|---|
| 2004/0217057 | A1* | 11/2004 | Rovatti | B01F 21/30 210/647 |
| 2007/0169825 | A1* | 7/2007 | Packham | A61M 39/26 137/614.05 |
| 2014/0190876 | A1* | 7/2014 | Meyer | A61M 1/3413 210/85 |
| 2016/0129174 | A1* | 5/2016 | Hundertmark | A61J 1/201 604/407 |

* cited by examiner

*Primary Examiner* — Dirk R Bass (57) ABSTRACT

The disclosure relates to systems and methods for generating a brine solution using a salt cartridge for recharging zirconium phosphate in a reusable sorbent module. The salt cartridge can include an inlet and an outlet on opposite sides. Water can be pumped through the salt cartridge to dissolve the salts in the salt cartridge and the resulting solution can be collected as a brine solution for use in recharging the zirconium phosphate.

13 Claims, 11 Drawing Sheets

AUTOMATIC RECHARGER BRINE PREPARATION FROM A SALT CARTRIDGE

FIELD

The disclosure relates to systems and methods for generating a brine solution using a salt cartridge for recharging zirconium phosphate in a reusable sorbent module. The salt cartridge can include an inlet and an outlet on a first and second side. Water can be pumped through the salt cartridge to dissolve the salts in the salt cartridge and the resulting solution can be collected as a brine solution for use in recharging the zirconium phosphate.

BACKGROUND

Sorbent based dialysis systems can use zirconium phosphate as a sorbent material to remove potassium, calcium, and magnesium ions from spent dialysate. The zirconium phosphate is generally provided in a sorbent cartridge with other sorbent materials. After use, the spent zirconium phosphate is disposed or removed from the sorbent cartridge for further processing. However, removing spent zirconium phosphate from a sorbent cartridge, separating the zirconium phosphate from other sorbent materials and processing the spent zirconium phosphate requires significant time and expense. Further, large quantities of solutions for processing the spent zirconium phosphate can be required along with the processing infrastructure, storage, and transportation. Expensive manufacturing lines and plants are required to generate pre-made solutions for use in processing the zirconium phosphate.

Hence, there is a need for systems and methods that can recharge zirconium phosphate within a reusable sorbent module. There is further a need for systems and methods for generating the recharge solutions necessary for recharging the zirconium phosphate, and in particular, brine solutions. There is a need for systems and methods that can generate the brine solution on-line and quickly, reducing the manufacturing burden, and reducing the storage needs and time required for preparation and recharging.

SUMMARY OF THE INVENTION

The problem to be solved by the present invention is online preparation of a brine solution for use in recharging sorbent materials. The solution can include sodium chloride and sodium acetate in a salt cartridge. The sodium chloride and sodium acetate can be dissolved when needed to generate the brine solution.

The first aspect of the invention relates to a system. In any embodiment, the system can include a sorbent recharger; the sorbent recharger having: i) a receiving compartment for a zirconium phosphate sorbent module; ii) at least a first fluid line fluidly connectable to an inlet of the zirconium phosphate sorbent module in the receiving compartment; iii) at least a second fluid line fluidly connectable to an outlet of the zirconium phosphate sorbent module; and iv) at least one pump. The system can also include a brine container fluidly connectable to the first fluid line; a salt cartridge; the salt cartridge having an inlet fluidly connectable to a water source and an acetic acid source; and an outlet fluidly connectable to the brine container; the salt cartridge containing sodium chloride and sodium acetate; and a control system; the control system programmed to: i) pump a preset volume of fluid from the water source through the salt cartridge; ii) recirculate fluid in a first flow path from the outlet of the salt cartridge to the brine container and then to the inlet of the salt cartridge; and to pump a preset volume of acetic acid into the first flow path.

In any embodiment, the inlet of the salt cartridge can be on a top of the salt cartridge, and the outlet of the salt cartridge can be on a bottom of the salt cartridge.

In any embodiment, the salt cartridge can include a first filter pad in the salt cartridge between the inlet of the salt cartridge and the sodium chloride and sodium acetate.

In any embodiment, the salt cartridge can include a filter pad in the salt cartridge between the sodium chloride and sodium acetate and the outlet of the salt cartridge.

In any embodiment, the salt cartridge can include a solution diversion base; wherein the outlet of the salt cartridge is below the solution diversion base.

In any embodiment, the control system can be further programmed to pump fluid from the brine container through the zirconium phosphate sorbent module.

In any embodiment, the control system can be programmed to recirculate fluid in the first flow path until a homogeneous solution is generated in the first flow path.

In any embodiment, the control system can be programmed to recirculate fluid in the first flow path for a preset period of time.

In any embodiment, the salt sodium chloride and sodium acetate can be initially solid.

In any embodiment, the sodium chloride and sodium acetate can be below a bottom of the inlet of the salt cartridge.

In any embodiment, the salt cartridge can include a spring-loaded valve at the inlet.

In any embodiment, the salt cartridge can include a spring-loaded valve at the outlet.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second, third, fourth, or fifth aspect of the invention described below, either alone or in combination, or follow any arrangement or permutation of any one or more of the described elements.

The second aspect of the invention relates to a method for generating a brine solution for recharging zirconium phosphate. In any embodiment, the method can include the steps of: pumping water from a water source to a salt cartridge through an inlet of the salt cartridge; the salt cartridge containing sodium chloride and sodium acetate; recirculating fluid from an outlet of the salt cartridge, to a brine container, and back to the inlet of the salt cartridge in a first flow path; pumping acetic acid into the first flow path; and collecting fluid from the first flow path into the brine container to generate the brine solution.

In any embodiment, the inlet of the salt cartridge can be on a top of the salt cartridge, and the outlet of the salt cartridge can be on a bottom of the salt cartridge.

In any embodiment, the salt cartridge can include a first filter pad in the salt cartridge between the inlet of the salt cartridge and the sodium chloride and sodium acetate.

In any embodiment, the salt cartridge can include a filter pad in the salt cartridge between the sodium chloride and sodium acetate and the outlet of the salt cartridge.

In any embodiment, the brine container can be fluidly connected to a sorbent recharger; and the method can include the step of pumping the brine solution through a zirconium phosphate sorbent module in the sorbent recharger.

In any embodiment, the fluid can be recirculated in the first flow path until a homogenous solution is generated.

In any embodiment, the fluid can be recirculated in the first flow path for a preset period of time.

In any embodiment, the salt sodium chloride and sodium acetate can be initially solid.

In any embodiment, the sodium chloride and sodium acetate can be below a bottom of the inlet of the salt cartridge.

In any embodiment, a top of the sodium chloride and sodium acetate can be about ¾ of an interior of the salt cartridge.

In any embodiment, the salt cartridge can include a solution diversion base; wherein the outlet of the salt cartridge is below the solution diversion base.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first, third, fourth, or fifth aspect of the invention, either alone or in combination, or follow any arrangement or permutation of any one or more of the described elements.

The third aspect of the invention is drawn to a salt cartridge for use in recharging zirconium phosphate. In any embodiment, the salt cartridge can include an inlet fluidly connectable to a water source; an outlet fluidly connectable to a brine container; and wherein the inlet is at a top of the salt cartridge and the outlet is at a bottom of the salt cartridge; the salt cartridge containing sodium chloride and sodium acetate.

In any embodiment, the salt cartridge can include a filter pad in the salt cartridge between the inlet of the salt cartridge and the sodium chloride and sodium acetate.

In any embodiment, the salt cartridge can include a filter pad in the salt cartridge between the outlet of the salt cartridge and the sodium chloride and sodium acetate.

In any embodiment, the salt cartridge can include a solution diversion base; wherein the outlet of the salt cartridge is below the solution diversion base.

In any embodiment, the salt cartridge can include a spring-loaded valve at the inlet.

In any embodiment, the salt cartridge can include a spring-loaded valve at the outlet.

The features disclosed as being part of the third aspect of the invention can be in the third aspect of the invention, either alone or in combination, or follow any arrangement or permutation of any one or more of the described elements. Similarly, any features disclosed as being part of the third aspect of the invention can be in the first, second, fourth, or fifth aspect of the invention, either alone or in combination, or follow any arrangement or permutation of any one or more of the described elements.

The fourth aspect of the invention is drawn to a sorbent recharger. In any embodiment, the sorbent recharger can include at least one inlet fluidly connectable to a water source; at least one inlet fluidly connectable to a brine container; and at least one outlet fluidly connectable to the salt cartridge of the third aspect of the invention.

In any embodiment, the sorbent recharger can include a control system programmed to: (i) pump a preset volume of fluid from the water source into the salt cartridge; (ii) recirculate fluid in a first flow path from the outlet of the salt cartridge to the brine container and then to the inlet of the salt cartridge; and to (iii) pump a preset volume of acetic acid into the first flow path.

In any embodiment, the control system can be programmed to recirculate fluid in the first flow path until a homogeneous solution is generated in the first flow path.

In any embodiment, the control system can be programmed to recirculate fluid in a first flow path for a preset period of time.

The features disclosed as being part of the fourth aspect of the invention can be in the fourth aspect of the invention, either alone or in combination, or follow any arrangement or permutation of any one or more of the described elements. Similarly, any features disclosed as being part of the fourth aspect of the invention can be in the first, second, third, or fifth aspect of the invention, either alone or in combination, or follow any arrangement or permutation of any one or more of the described elements.

The fifth aspect of the invention is drawn to a brine container. In any embodiment, the brine container can include an inlet fluidly connectable to the salt cartridge of the third aspect of the invention; and an outlet fluidly connectable to a sorbent recharger.

The features disclosed as being part of the fifth aspect of the invention can be in the fifth aspect of the invention, either alone or in combination, or follow any arrangement or permutation of any one or more of the described elements. Similarly, any features disclosed as being part of the fifth aspect of the invention can be in the first, second, third, or fourth aspect of the invention, either alone or in combination, or follow any arrangement or permutation of any one or more of the described elements.

DETAILED DESCRIPTION

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "above" refers to a component that is at a higher elevation than another component when arranged for ordinary use.

"Acetic acid" refers to $CH_3CO_2H$ in an aqueous solution.

An "acetic acid source" can be a solid, fluid, or concentrate source from which acetic acid or an acetic acid solution can be obtained.

The term "below" refers to a component that is at a lower elevation than another component when arranged for ordinary use.

The term "bottom" refers to a portion of a component intended to be at a lower elevation than a "top" during normal use of the component.

A "brine container" is a container for containing a brine solution.

A "brine solution" is a solution containing sodium chloride, an acid, and the sodium salt of the acid.

To "collect" a fluid can refer to flowing a volume of the fluid into a container.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The term "containing" refers to a substance that is within a component or container.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain performance specifications.

A "filter pad" can be a porous pad through which water or aqueous solutions can pass, but that prevents solid materials from passing.

A "flow path" is a pathway through which a fluid, gas, or any combination or mixture thereof can travel.

A "fluid" is a liquid substance optionally having a combination of gas and liquid phases in the fluid. Notably, a liquid, as used herein, can therefore also have a mixture of gas and liquid phases of matter.

A "fluid line" can refer to a tubing or conduit through which a fluid or fluid containing gas can pass. The fluid line can also contain air during different modes of operation such as cleaning or purging of a line.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

The terms "generate," "generating," "is generated," and the like refer to forming a solution or substance from constituent parts.

The term "homogeneous solution" refers to an aqueous solution wherein the concentration of solutes is substantially identical at all parts of the solution.

The term "initially" refers to a state of a component or system prior to a process.

The term "inlet" can refer to a portion of container, flow path, or component through which fluid, gas, or a combination thereof can be drawn into the container, flow path, or component.

The term "interior" refers to an area inside of a given component or system.

The term "outlet" can refer to a portion of container, flow path, or component through which fluid, gas, or a combination thereof can be drawn out of the container, flow path, or component.

A "preset period of time" is a length of time that is set prior to a process or step.

The term "preset volume" refers to an amount of fluid determined prior to a process.

The term "programmed," when referring to a processor, can mean a series of instructions that cause a processor to perform certain steps.

The term "pump" refers to any device that causes the movement of fluids or gases by applying suction or pressure.

A "receiving compartment" can be a compartment, section, or chamber of any device or components. In one non-limiting example, the receiving compartment can be within a sorbent recharger into which a sorbent module can be positioned to be recharged.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

To "recirculate" refers to moving fluid in a flow loop from a first point through the flow loop and back to the first point.

A "salt cartridge" is a container designed to hold solid salts for generation of a brine solution. The salt cartridge can include an inlet on one side for receiving water and an outlet on the opposite side for the formed solution to exit. Fluid can enter the salt cartridge and dissolve the salts to generate the brine solution as the fluid passes through the salt cartridge.

The term "sodium acetate" refers to $CH_3CO_2Na$ either solid or in an aqueous solution.

The term "sodium chloride" refers to NaCl either solid or in an aqueous solution.

The term "solid" refers to a material in the solid phase of matter, and can include crystalline, powdered, or any other form of solid material.

A "solution diversion base" is a bottom of a component or cartridge that has one or more features causing fluid to flow in a specified pattern. The solution diversion base can cause fluid to evenly disperse over a given area.

A "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module"

generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

A "sorbent recharger" or "recharger" is an apparatus designed to recharge at least one sorbent material.

A "spring-loaded valve" is a valve controlled by a spring, the valve opens or closes when pressure is placed on the spring.

The term "top" refers to a portion of a component intended to be at a higher elevation than a "bottom" during normal use of the component.

The term "water source" refers to any source from which potable or non-potable water can be obtained.

"Zirconium phosphate" is a sorbent material that removes cations from a fluid, exchanging the removed cations for different cations.

A "zirconium phosphate sorbent module" is a sorbent module that contains zirconium phosphate.

Brine Preparation from a Salt Cartridge

Figure 1A:
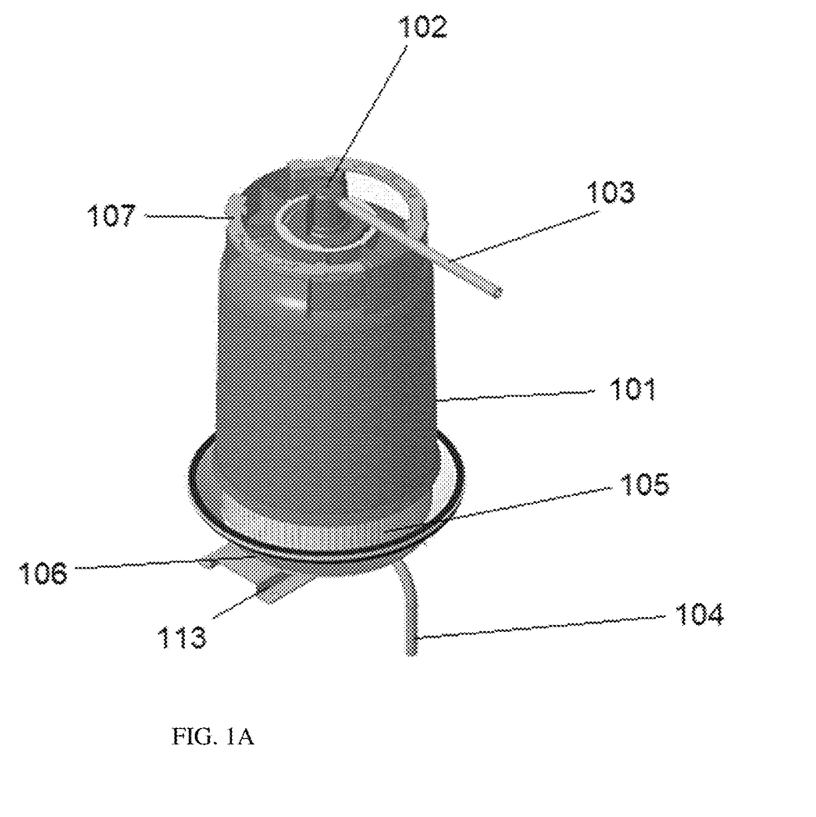
FIGS. 1A-I illustrate a salt cartridge for preparation of a brine solution.
Figure 1B:
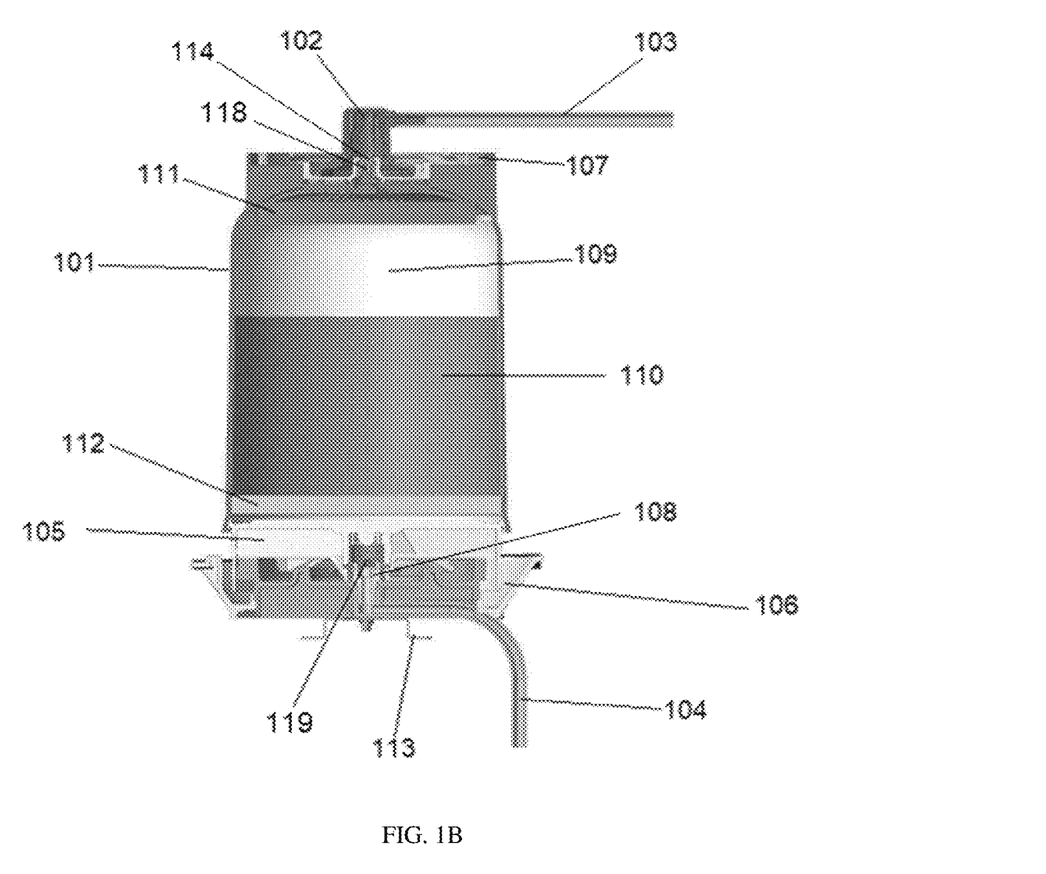
Figure 1C:
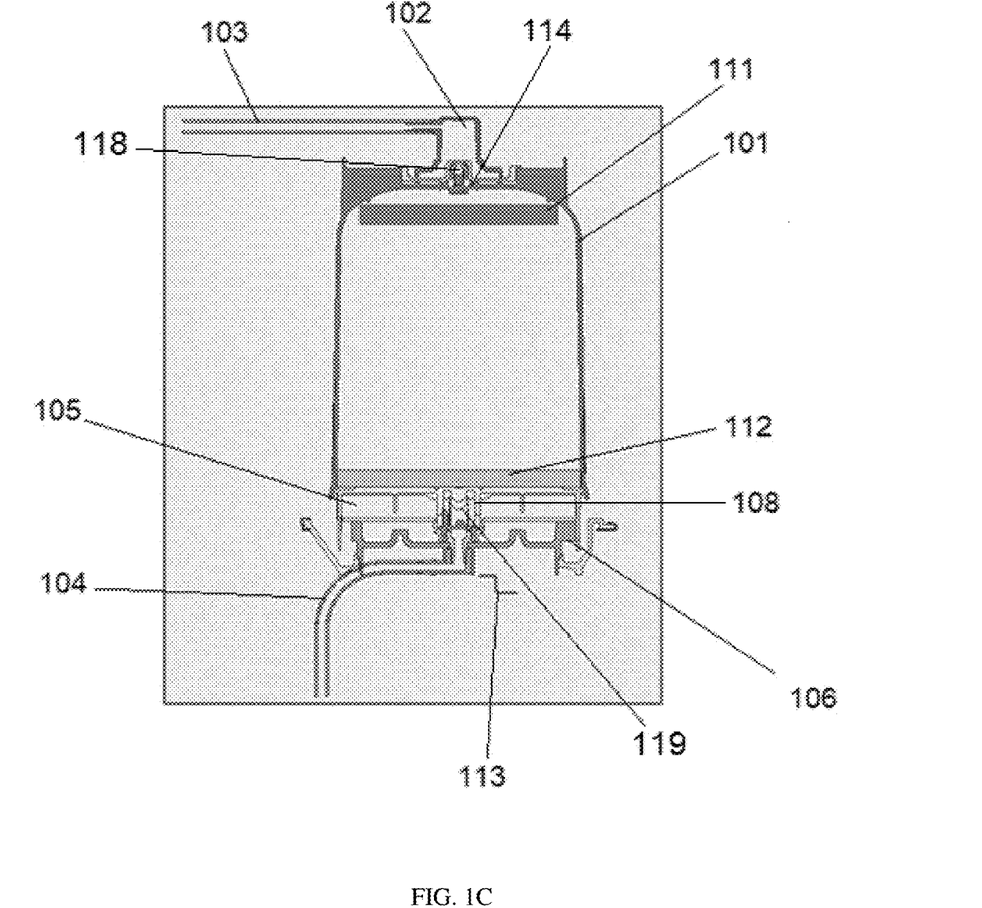
Figure 1D:
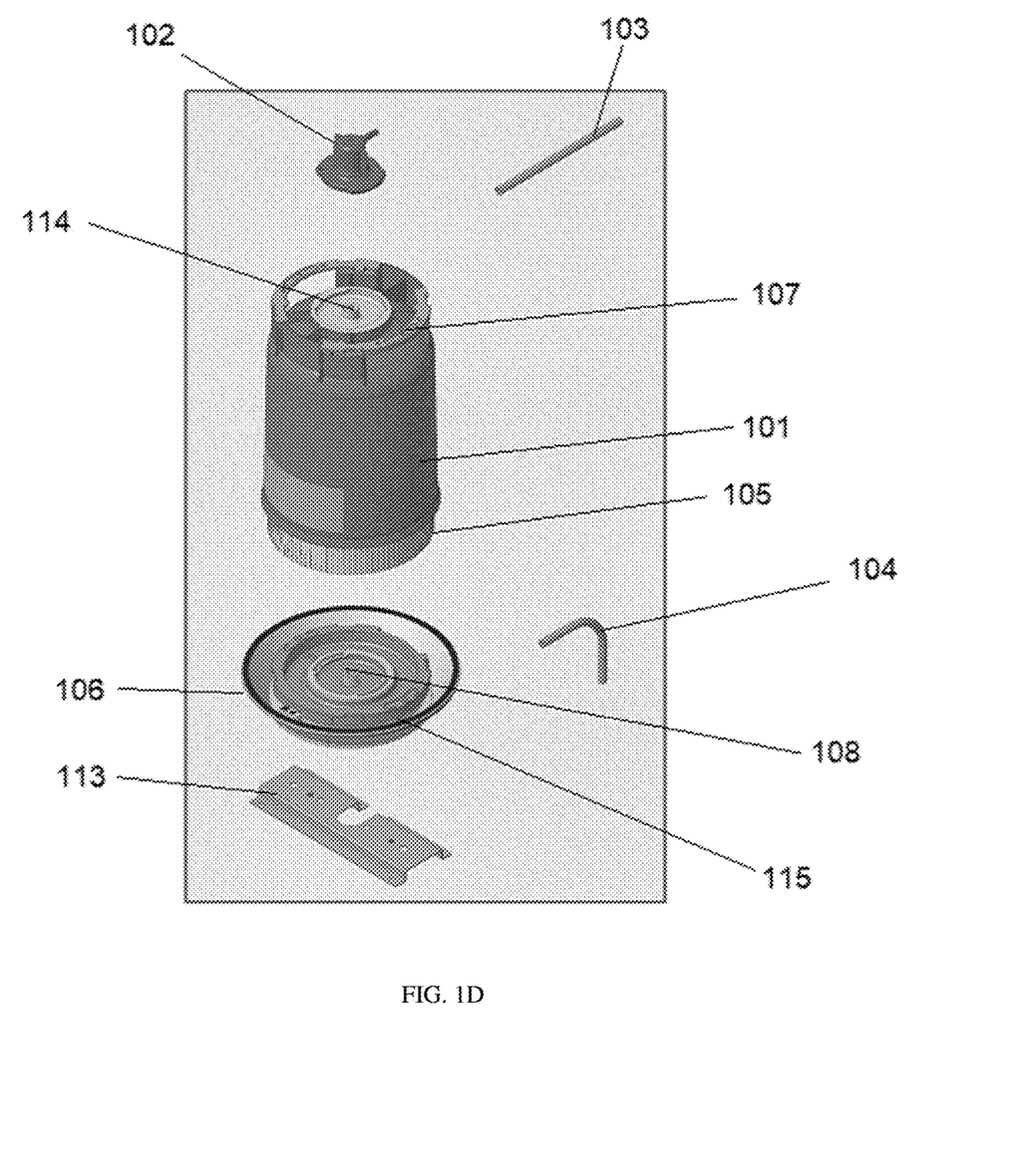
Figure 1E:
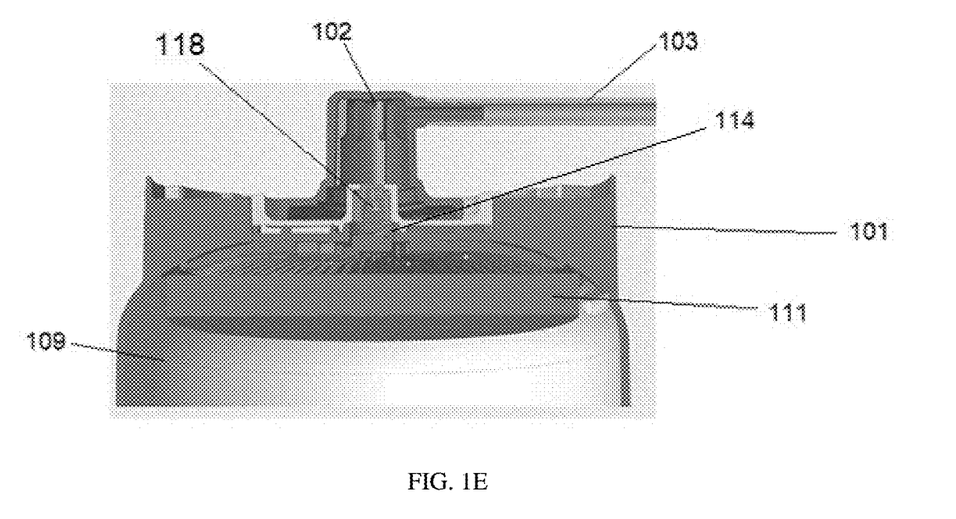
Figure 1F:
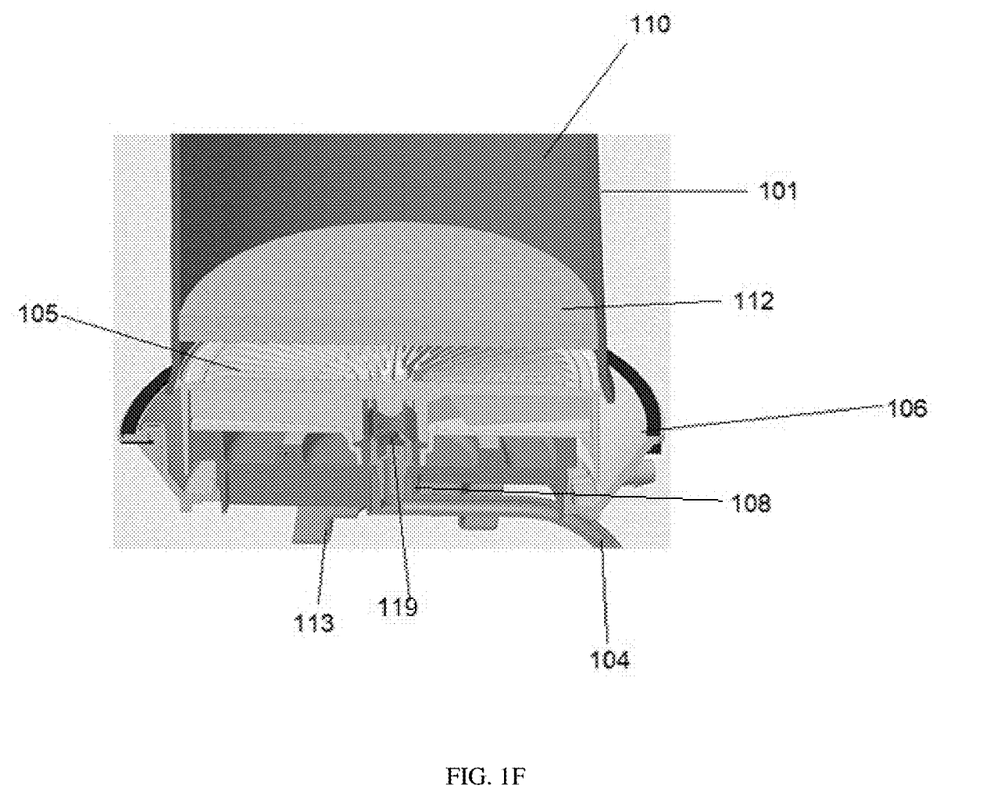
Figure 1G:
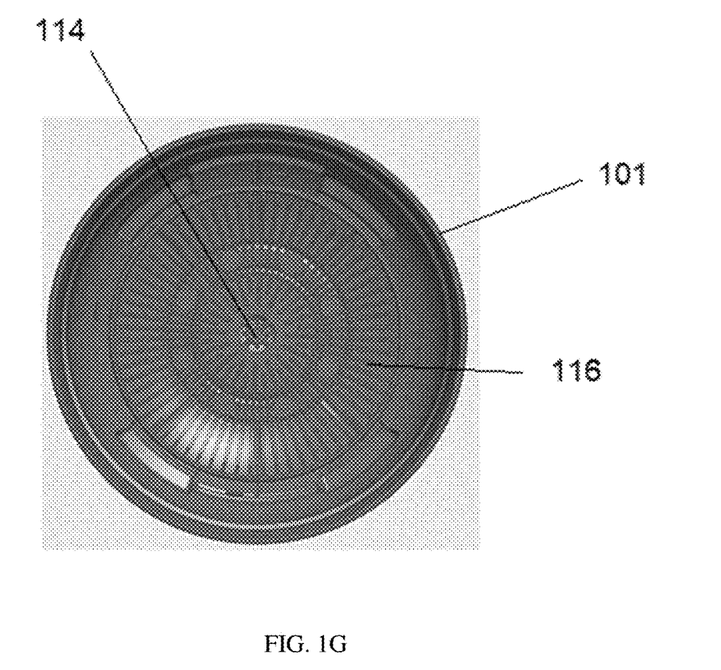
Figure 1H:
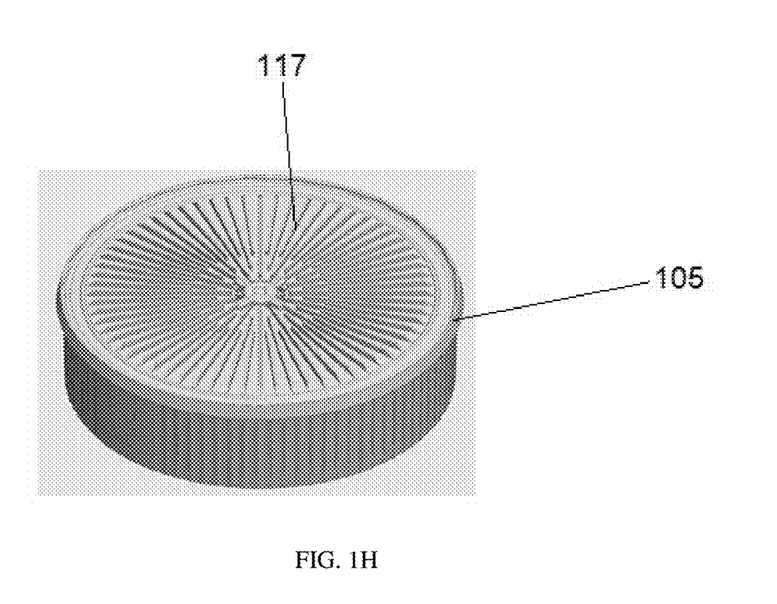
Figure 1I:
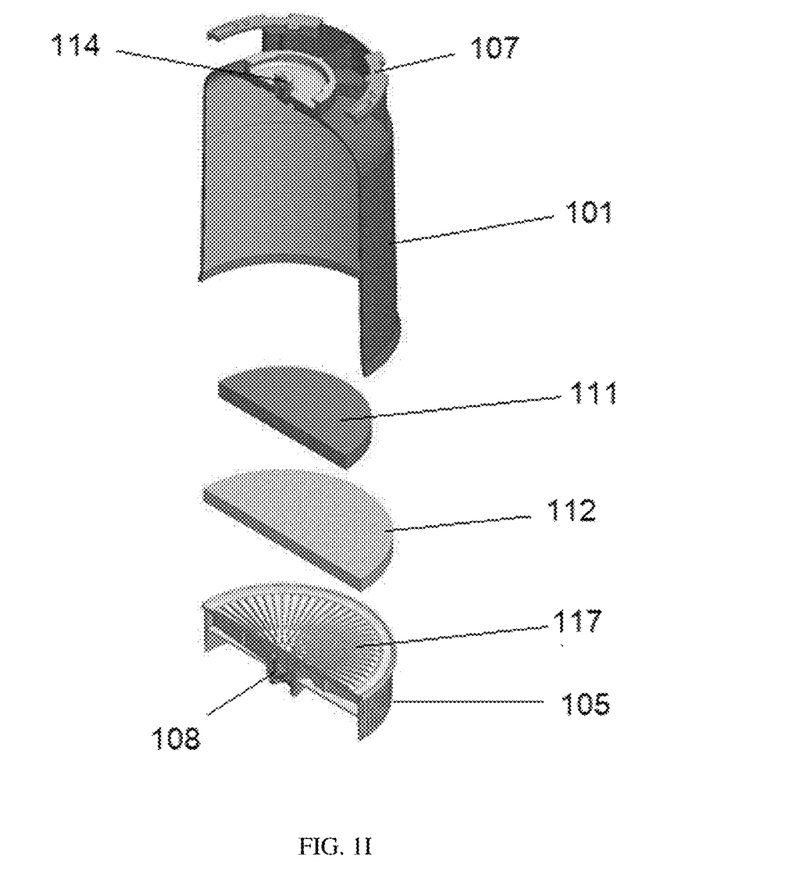

FIGS. 1A-I illustrate a salt cartridge 101 that can be used to generate brine for recharging zirconium phosphate in a reusable zirconium phosphate sorbent module. FIG. 1A is a perspective view of a salt cartridge 101; FIG. 1B is a front transparent view of the salt cartridge 101, FIG. 1C is a rear transparent view of an empty salt cartridge 101, FIG. 1D is an exploded view of the connections to the salt cartridge 101, FIG. 1E is a transparent close up view of a top of the salt cartridge 101, FIG. 1F is a transparent close up view of the bottom of the salt cartridge 101, FIG. 1G is a close up view of a top of the salt cartridge 101, FIG. 1H is a close up view of a base of the salt cartridge 101, and FIG. 1I is an exploded view of the salt cartridge 101.

FIG. 1A shows the salt cartridge 101 mounted on a base frame 106. A base 105 of the salt cartridge 101 can be inserted into the base frame 106 for mounting. A bracket 113 can be included to mount the base frame 106 on a surface or a recharger. The salt cartridge can include a connector 102 positioned at a top of the salt cartridge 101 for connection to a fluid line 103. Water can be pumped into the salt cartridge 101 through the fluid line 103. An additional connector (not shown in FIG. 1A) can connect to fluid line 104 positioned at a bottom of the salt cartridge 101 for brine solution to be pumped out of salt cartridge 101.

As illustrated in FIG. 1B, the salt cartridge 101 can include an inlet 114 at the top of the salt cartridge 101 and an outlet 108 at the bottom of salt cartridge 101. Fluid can flow downwardly through salt cartridge 101 from the inlet 114 to the outlet 108. The inlet 114 can connect to connector 102, which in turn connects to fluid line 103, which is fluidly connectable to both a water source and an acetic acid source (not shown). The outlet 108 can connect to fluid line 104, which is fluidly connectable to a brine container (not shown). Initially solid salts 110 can be placed in the salt cartridge 101. A top portion 109 of the salt cartridge 101 can initially be empty. To generate a brine solution, water can be pumped into the salt cartridge 101. The water passes through a first filter pad 111. The water wets the entire filter pad 111 and drops onto the solid salts 110. In certain embodiments, the filter pad 111 can be a foam filter. Other materials known to those of skill in the art can be used for the filter pad 111 as well. Because filter pad 111 is wider than the inlet 114, the water distribution on the salts 110 is uniform, causing smooth and uniform soaking of the salts 110. The water can dissolve the sodium chloride and sodium acetate in the salt cartridge 101 and exit through outlet 108. A second filter pad 112 can be included to prevent larger solid particles from entering outlet 108 or fluid line 104 connected to outlet 108. The filter pad 112 can be placed between the solid salts 110 and the outlet 108 to filter brine solution exiting the salt cartridge 101. Fluid travels through the salt cartridge 101 from inlet 114 to outlet 108, dissolving the salts within the salt cartridge 101 as the fluid flows downwardly through the salt cartridge 101.

After the brine solution exits through the outlet 108 of salt cartridge 101 into fluid line 104, the generated brine solution can be collected in the brine container (not shown). The brine solution can be recirculated back to inlet 114 of the salt cartridge 101, through the outlet 108, and back through the brine container. The brine solution can be recirculated for a preset period of time, or until full dissolution of the solid salts 110 and after a homogeneous solution is formed in the recirculation flow path. As illustrated in FIG. 1B, the salt cartridge 101 can initially be filled about ¾ full with solid salts 110, leaving about ¼ of the volume of the salt cartridge 101 in the top portion 109 available for filling with water. This places the salts 110 below the bottom of inlet 114. However, the actual amount of solid salts initially placed in salt cartridge 101 can vary. For example, the salt cartridge 101 can initially be ½ filled, ⅔ filled, ¼ filled or any other fractional amount depending on the needs of the user.

FIG. 1C is a transparent view of the salt cartridge 101, including inlet 114 at the top of the salt cartridge 101 and an outlet 108 at the bottom of salt cartridge 101. The salt cartridge 101 includes a first filter pad 111 at a top portion of the salt cartridge 101 and a second filter pad 112 in the bottom portion of the salt cartridge 101. The inlet 114 and outlet 108 can include spring loaded valve 118 and spring-loaded valve 119, respectively. The spring-loaded valves prevent the salt inside the salt cartridge 101 from spilling out. When the salt cartridge 101 is not connected to the system, spring loaded valve 118 and spring-loaded valve 119 are closed. When the salt cartridge 101 is connected to the base frame 106, pressure is applied to the top and bottom of the salt cartridge 101, opening spring loaded valve 118 and spring-loaded valve 119 to allow fluid into and out of the salt cartridge 101. Upon connection, connector 102 at the inlet 114 and a connector connecting fluid line 104 to outlet 108 can act similar to plungers, opening spring loaded valve 118 and spring-loaded valve 119 to assist fluid flow. Spring loaded valve 118 and spring-loaded valve 119 also operate as non-return valves during salt preparation. Fluid flow in an out of the salt cartridge 101 can be arrested due to spring loaded valve 118 and spring-loaded valve 119.

FIG. 1D is an exploded view of the salt cartridge 101. The base 105 of the salt cartridge 101 can be inserted into base frame 106. Connector 102 can connect inlet 114 to fluid line 103. Fluid line 104 can connect to outlet 108. The base frame 106 can include an opening in the bottom to allow fluid line 104 to connect to the salt cartridge 101. Frame 107 houses the base frame 106 or cartridge holder of the salt cartridge 101 can be included for carrying or moving the salt cartridge 101. The base frame 106 can be included to mount the salt cartridge 101. The base frame 106 holds a bottom 115 the salt cartridge 101 in place during use and provides a space underneath the salt cartridge 101 for connection to fluid line 104. As illustrated in FIG. 1D, a bracket 113 can be included to mount the base frame 106 on a surface or a recharger. The base frame 106 acts as a cartridge holder to hold salt cartridge 101 in place an apply pressure to spring loaded valves (not shown in FIG. 1D). However, as understood by a person of ordinary skill in the art, alternative methods of mounting the salt cartridge 101 can be used, including hooks or any other method.

FIG. 1E is a close-up view of a top of the salt cartridge 101. Spring-loaded valve 118 is compressed as pressure is applied when connector 102 is attached to the inlet 114. The compression of spring-loaded valve 118 allows fluid to flow through fluid line 103 and into the salt cartridge 101. The fluid wets filter pad 111, evenly distributing fluid across the salt cartridge 101.

FIG. 1F is a close-up view of a bottom of the salt cartridge 101. Spring-loaded valve 119 is compressed as pressure is applied when fluid line 104 is connected to outlet 108. The compression of spring-loaded valve 119 allows fluid to flow through fluid line through the outlet 108 and into fluid line 104. Filter pad 112, prevents large salt particles from exiting the salt cartridge 101 while allowing the generated brine solution through. The filter pad 112 can be any type of filter known to those of skill in the art that will prevent most solid salt particles from passing through while allowing the brine solution to pass through.

FIG. 1G shows a top of the salt cartridge 101, including inlet 114. The top of the salt cartridge 101 can include ridges 116 to help evenly distribute fluid entering through inlet 114. The ridges 116 can extend radially from a desired point, such as inlet 114, to induce flow to the desired point. In certain embodiments, the top of the salt cartridge 101 can have a slightly concave or convex surface to induce flow to the desired point. The ridges 116 can be uniform in length or have different lengths.

As illustrated in FIG. 1H, the base 105 of salt cartridge 101 can be a solution diversion base that includes solution diversion ridges 117. The solution diversion ridges 117 can be positioned above the outlet 108. The solution diversion ridges 117 ensure that flow through the salts is even, causing the entire column of sodium chloride and sodium acetate to contact the water and dissolve. The diversion ridges 117 can be uniform in length or have different lengths. In certain embodiments, the base 105 can have a slightly concave or convex surface to induce flow to the desired point.

FIG. 1I is an exploded cutaway view of the salt cartridge 101. The salt cartridge 101 can include a frame 107 at a top of the salt cartridge 101. The first filter pad 111 is placed between the inlet 114 and a top level of salt in the salt cartridge 101. Second filter pad 112 is placed at the bottom of the salt cartridge 101 above outlet 108. The base 105 of the salt cartridge 101 includes solution diversion ridges 117 to ensure even flow of fluid through the salt column.

The salt cartridge 101 can be constructed from any material known to those of ordinary skill capable of holding the salts 110. In certain embodiments, the salt cartridge 101 can be constructed from a polymer such as polypropylene, polyethylene, or high-density polyethylene. Alternatively, metal, glass, or other materials can be used.

One of skill in the art will understand that the required size of the salt cartridge 101 depends on the amount of brine solution desired. As a non-limiting example, the salt cartridge 101 can be sized to hold between 1.5-2.0 kg of sodium acetate and sodium chloride with 200-300 mL left of water filling capacity. The volume of water added can be varied to generate a brine solution having a desired sodium concentration. In certain embodiments, about 5 L of water can be used to generate the brine solution. However, with larger brine outputs desired, the salt cartridge can be made larger as well. The volume of water added can be varied to generate a brine solution having a desired sodium concentration. In certain embodiments, about 5 L of water can be used to generate the brine solution. However, the amount of water used can be varied depending on the desired brine solution concentration and the amount of salt used.

Figure 2:
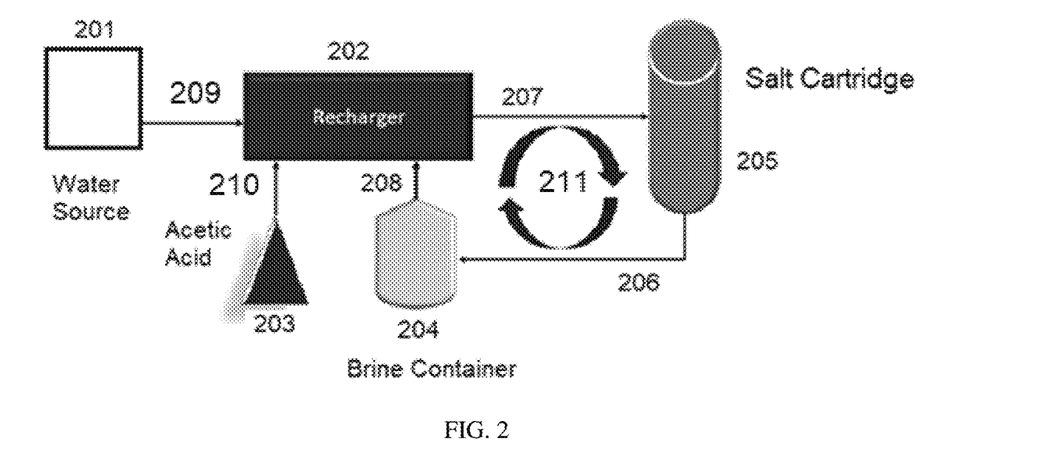
FIG. 2 illustrates a sorbent recharger system using a salt cartridge.

FIG. 2 is a generalized diagram of a sorbent recharger system using the described salt cartridge 205. As described, a salt cartridge 205 can contain sodium acetate and sodium chloride in any amounts. Water from water source 201 can be pumped into an inlet of the salt cartridge 205. In certain embodiments, the water source can be fluidly connected to a sorbent recharger 202. The water can be pumped from water source 201, through line 209 into the sorbent recharger 202 and then into the salt cartridge 205 through fluid line 207. Alternatively, a separate fluid line (not shown) can connect the water source 201 to the inlet of salt cartridge 205.

The water pumped into salt cartridge 205 can dissolve the sodium acetate and sodium chloride and exit through an outlet of the salt cartridge 205 into brine container 204. To ensure complete dissolution of the sodium acetate and sodium chloride and a homogeneous brine solution, the solution can be recirculated through a flow path as shown by arrows 211. The brine solution can be pumped from the outlet of the salt cartridge 205 into brine container 204 through fluid line 206, back into sorbent recharger 202 through fluid line 208, and then back to the inlet of the salt cartridge 205 through fluid line 207. The salt cartridge 205, fluid line 206, brine container 204, fluid line 208, sorbent recharger 202, and fluid line 207 define a recirculation flow path. The solution can be pumped through the recirculation flow path until a homogeneous solution is formed, or for some preset period of time that is long enough to ensure formation of a homogenous solution. The preset period of time can be any time long enough to ensure complete dissolution and homogeneity. In certain embodiments, the preset period of time can be between 20 and 45 minutes. Additionally, or alternatively, one or more sensors, such as conductivity sensors, can be included to ensure that the generated brine solution has the proper concentrations of sodium chloride and sodium acetate.

The brine solution, once formed, can be used to recharge zirconium phosphate in a zirconium phosphate sorbent module. The brine solution can replace cations that were bound to the zirconium phosphate during dialysis treatment with sodium and hydrogen ions. The final ratio of sodium to hydrogen ions on the recharged zirconium phosphate is a function of the pH and sodium concentration of the brine solution. As such, the sodium/hydrogen ratio of the recharged zirconium phosphate can be controlled by controlling the pH and sodium concentration of the brine solution used in recharging. Acetic acid from acetic acid source 203 can be added to the recirculation flow path while the brine is being recirculated to adjust the pH of the brine solution. Acetic acid can be pumped from acetic acid source 203 through fluid line 210 into the sorbent recharger 202 for addition to the recirculating flow path. A control system (not shown) can control one or more pumps and one or more valves within the sorbent recharger 202 to generate a brine solution having a specified pH by adding a volume of acetic acid from the acetic acid source 203. Using a known amount of sodium chloride and sodium acetate in salt cartridge 205 and adding a set amount of water from water source 201 can provide a known sodium concentration in the resulting brine solution. The amount of acetic acid added from acetic acid source 203 can be controlled by the control system to generate a brine solution having a desired pH.

To recharge the zirconium phosphate in a zirconium phosphate sorbent module, the control system can control one or more pumps (not shown) and/or valves (not shown)

to pump the generated brine solution from brine container 204, through fluid line 208, into sorbent recharger 202 where the brine solution is passed through the zirconium phosphate sorbent module.

Table 1 shows a non-limiting example of a brine solution for recharging zirconium phosphate that can be made using the described salt cartridge system.

TABLE 1

ZP Recharge- Brine Solution Preparation

| Description | Sodium chloride | Sodium Acetate, trihydrate | Acetic Acid | Water |
|---|---|---|---|---|
| Conc M | 4.70 | 0.40 | 0.40 | N/A |
| Mol wt | 58.50 | 136.00 | 60.05 | N/A |
| Mix density (kg/l) @25° C. | | 1.19 | | |
| Individual density (kg/l) @25° C. | 2.16 | 1.45 | 1.05 | 1.00 |
| Total Volume (L) | | 6.20 | | |
| Total weight (kg) | | 7.38 | | |
| Individual weight (kg) | 1.70 | 0.34 | 0.15 | 5.19 |
| Individual volume (L) | N/A | N/A | 0.14 | 5.20 |

The brine solution described in Table 1 uses 5.20 L of water, which is added to a salt cartridge containing 1.70 kg of sodium chloride and 0.34 kg of sodium acetate trihydrate. 0.14 L of acetic acid can be added during generation of the brine solution, as described. The resulting brine solution has a sodium chloride concentration of 4.70 M, a sodium acetate concentration of 0.40 M, and an acetic acid concentration of 0.40 M. However, as described, brine solutions having a higher or lower pH can be generated by adding more or less acetic acid or sodium acetate. A person of ordinary skill in the art will understand that the ratio of sodium chloride to sodium acetate used can vary depending on the needs of the user. The sodium concentration of the brine solution can be controlled by using more or less sodium chloride and sodium acetate or by varying the volume of water added to the salt cartridge in forming the brine solution as would be understood by one of ordinary skill in the art. One or more conductivity sensors can be used to ensure complete dissolution and homogeneity. The conductivity of the generated brine solution will vary based on the concentrations of each solute. However, the conductivity of the solution shown in Table 1 should be within 180-240 mS/cm at 25° C.

Figure 3A:
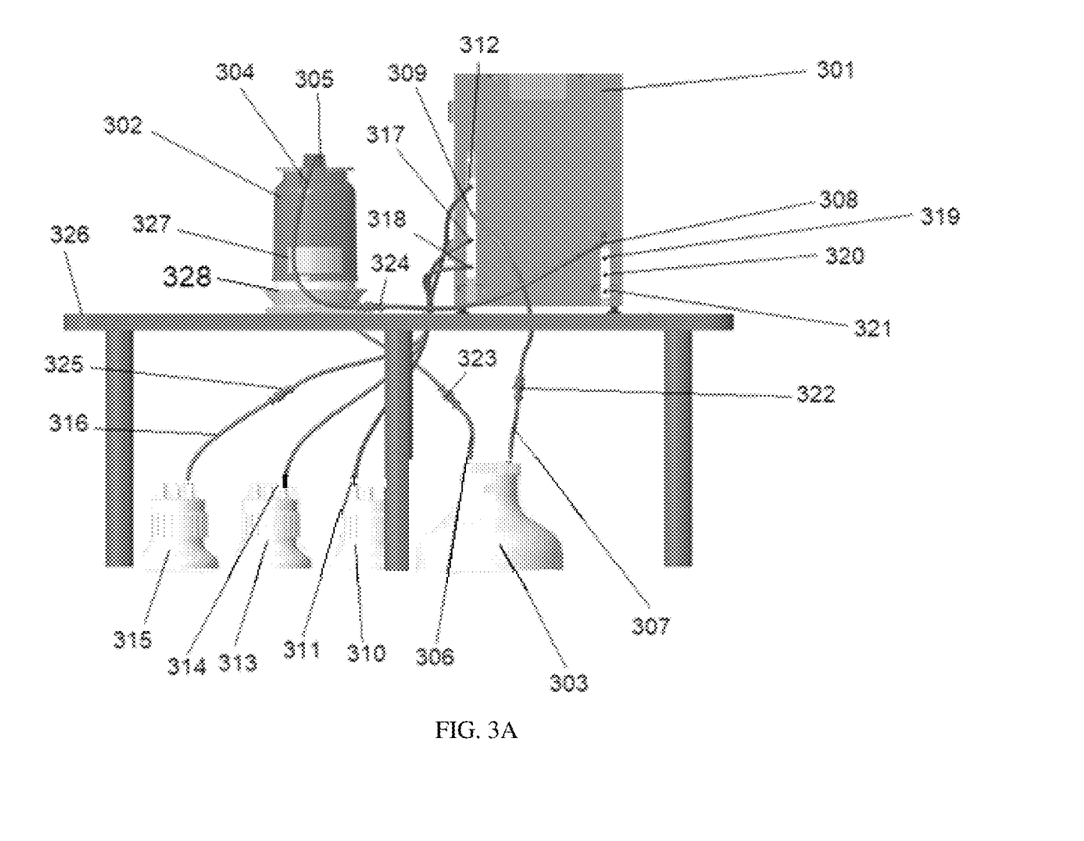
FIGS. 3A-C illustrate a sorbent recharger for recharging sorbent materials in reusable sorbent modules.
Figure 3B:
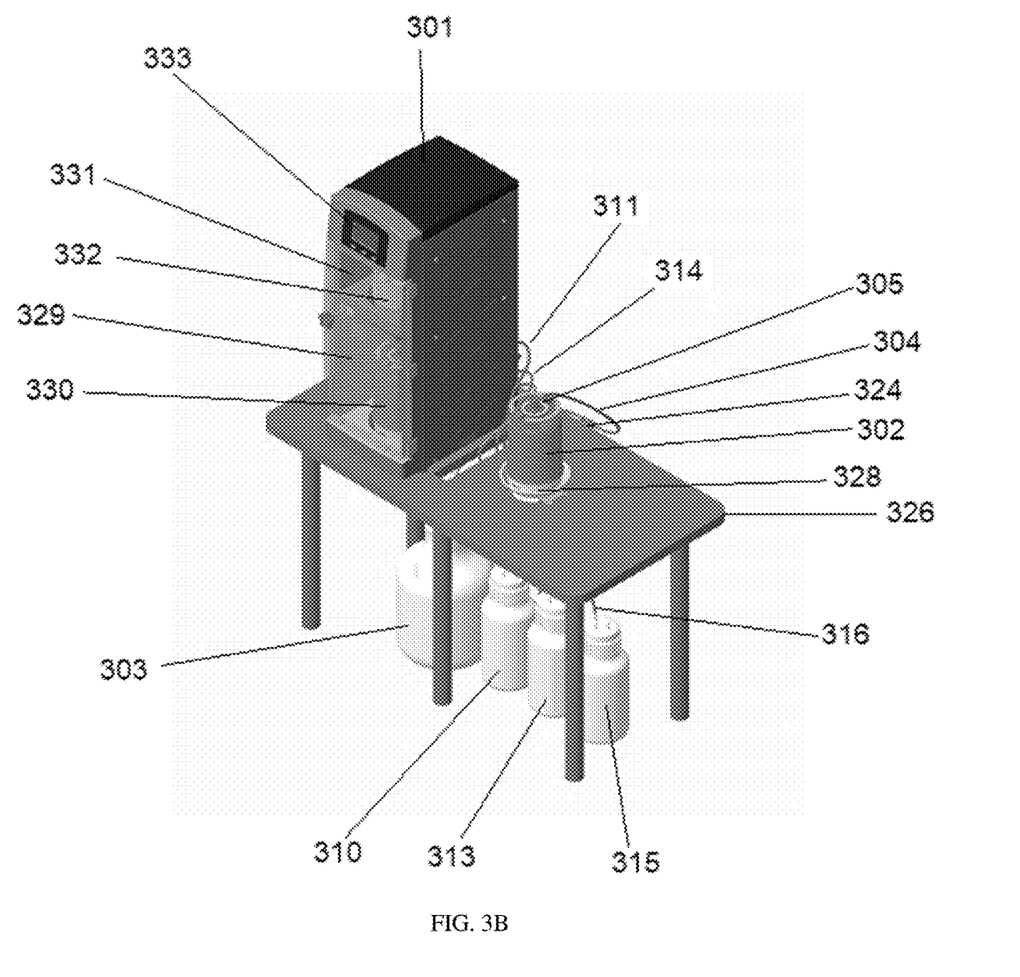
Figure 3C:
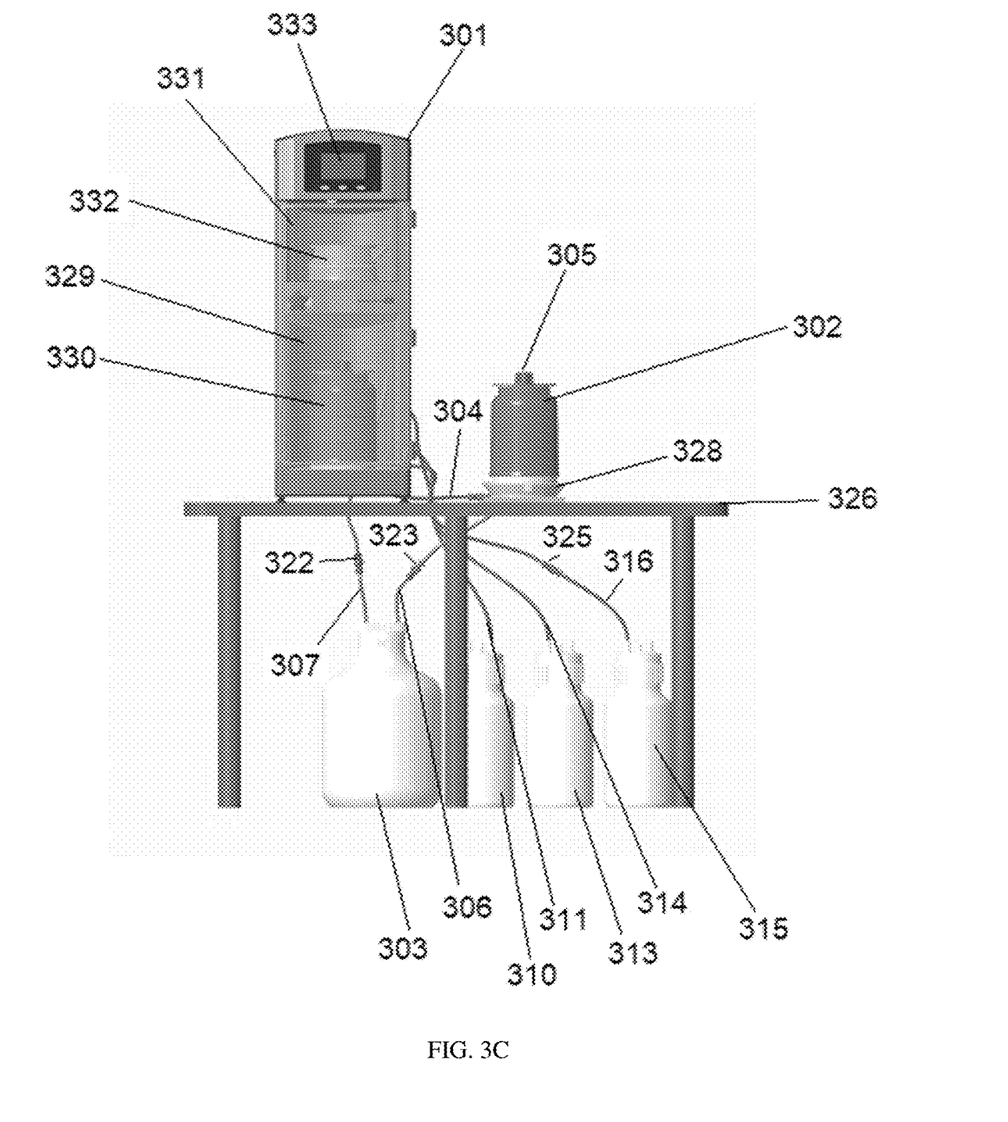

FIGS. 3A-C show a sorbent recharger 301 using a salt cartridge 302 as described. FIG. 3A is a rear view of the sorbent recharger 301, FIG. 3B is a perspective view of the sorbent recharger 301, and FIG. 3C is a front view of the sorbent recharger 301. As illustrated in FIG. 3A, the salt cartridge 302 can be fluidly connected to the sorbent recharger 301. Water from a water source (not shown) can be pumped through an inlet 305 of the salt cartridge 302 containing sodium chloride and sodium acetate through fluid line 304. The brine solution formed can exit the salt cartridge 302 through an outlet (not shown) and flow through fluid line 306 into brine container 303. Fluid can be recirculated in a flow path from the outlet of the salt cartridge 302, through fluid line 306 and into the brine container 303, out of brine container 303 through fluid line 307 back to sorbent recharger 301 through inlet port 309, and then through outlet port 308 back into the salt cartridge 302 through fluid line 304. The brine solution can be recirculated in the flow path until a homogeneous solution is formed, or for a preset period of time. While the brine solution is recirculating, acetic acid from acetic acid source 310 can be pumped through fluid line 311 into sorbent recharger 301 through inlet port 312, where the acetic acid is added to the recirculating brine solution. After a homogeneous brine solution is formed, the brine solution can be collected in brine container 303.

As described, in certain embodiments, the sorbent recharger can also be used to recharge zirconium oxide. To recharge zirconium oxide, a basic solution can be pumped through the zirconium oxide. Sodium hydroxide from sodium hydroxide source 313 can be pumped through fluid line 314 into sorbent recharger 301 through inlet port 317 and through the zirconium oxide sorbent module 332. Bleach from bleach source 315 can be pumped through fluid line 316 into sorbent recharger 301 through inlet port 318 and through the zirconium oxide sorbent module 332 to disinfect the zirconium oxide sorbent module 332.

As illustrated in FIG. 3A, the sorbent recharger 301 can include fluid inlet port 309 for receiving a brine solution, inlet port 312 for receiving acetic acid, inlet port 317 for receiving sodium hydroxide, and inlet port 318 for receiving bleach. An additional inlet port (not shown) can be included for receiving water from a water source (not shown). The sorbent recharger 301 can also include outlet port 308 for pumping fluid to the salt cartridge 302. Additional outlet ports, including outlet port 319, outlet port 320, and outlet port 321 can be included for connection to a drain, waste container, or collection container.

The salt cartridge 302 can connect to fluid lines 306 and 308 through any means known in the art. In FIG. 3A, the connections are shown as a quick connector 324 to connect to the sorbent recharger 301 and quick connector 323 to connect to brine container 303. A similar quick connector 322 can be used to connect brine container 303 to the sorbent recharger 301 and quick connector 325 can connect bleach source 315 to fluid line 316. One of skill in the art will understand that connectors can also be used for connecting any of the fluid sources to the fluid lines. Quick connectors allow fluid lines to be connected by snapping connectors on each line together. However, other connectors that can form fluid passages can be used. As described, the salt cartridge 302 can be mounted on the system using base plate 328, or by any other method. In certain embodiments, identification plate 327 can be included on the salt cartridge 302 to identify a specific salt cartridge or to display any other information.

As illustrated in FIG. 3B, The sorbent recharger 301 can include one or more receiving compartments for receiving reusable sorbent modules. The sorbent recharger 301 includes a first receiving compartment 329 for receiving a zirconium phosphate sorbent module 330. To recharge the zirconium phosphate in the zirconium phosphate sorbent module 330, the generated brine solution in brine container 303 is pumped through the zirconium phosphate sorbent module 330, replacing potassium, calcium, magnesium, and ammonium ions bound to the zirconium phosphate with sodium and hydrogen ions.

In certain embodiments, additional receiving compartments can be included. For example, the sorbent recharger 301 shown in FIG. 3B includes a second receiving compartment 331 for receiving a zirconium oxide sorbent module 332. Additional chemicals can be included for recharging the zirconium oxide in zirconium oxide sorbent module 332. To recharge zirconium oxide, sodium hydroxide from sodium hydroxide source 313 can be pumped through fluid line 314 into sorbent recharger 301 and through the zirconium oxide sorbent module 332. Bleach from bleach source 315 can be pumped through fluid line 316 into sorbent recharger 301 and through the zirconium oxide sorbent module 332 to disinfect the zirconium oxide sorbent module 332. Alternatively, a sorbent recharger can include two receiving compartments to recharge two different zirconium phosphate sorbent modules. In any embodiment, the sorbent recharger 301 can include any number of receiving compartments for recharging any number of zirconium phosphate and/or zirconium oxide sorbent modules.

The sorbent recharger can include a graphical user interface 333 shown in FIG. 3B that can be used to control recharging of the sorbent materials. Through graphical user interface 333, the user can initiate, stop, and otherwise control the preparation of the brine solution and the recharging process. Further, any errors, alerts, or other messages can be provided to the user through graphical user interface 333. In FIG. 3B, the sorbent recharger 301 is small enough to fit on table 326. However, larger sorbent rechargers can be used for recharging additional materials.

FIG. 3C shows a front view of the sorbent recharger 301. The sorbent recharger 301 includes a first receiving compartment 329 for receiving a zirconium phosphate sorbent module 330 and a second receiving compartment 331 for receiving a zirconium oxide sorbent module 332. Brine container 303 is connected to an outlet of the salt cartridge 302 through fluid line 306 having quick connector 323. The brine container is also connected to sorbent recharger 301 through fluid line 307 having quick connector 322. To generate a brine solution, fluid is recirculated between the salt cartridge 302, brine container 303 and sorbent recharger 301 until a homogeneous solution is formed. Acetic acid source 310, sodium hydroxide source 313 and bleach source 315 can each be connected to sorbent recharger 301 through fluid lines 311, 314, and 316, respectively. As described, the sorbent recharger 301 can include graphical user interface 333 for controlling the recharging process.

Figure 4:
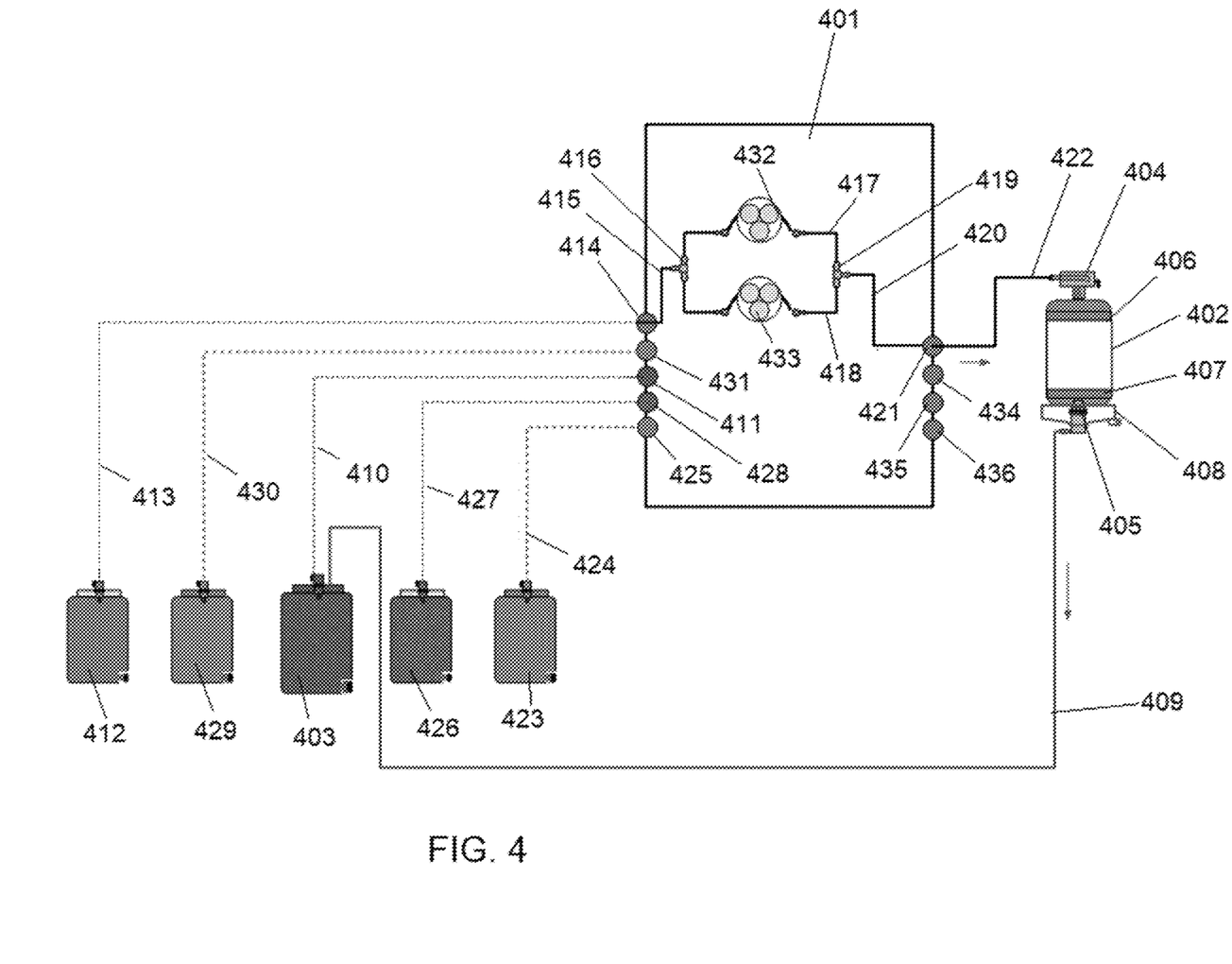
FIG. 4 shows a flow path for a sorbent recharger using a salt cartridge.

FIG. 4 shows a flow diagram for a recharger system using a salt cartridge. salt cartridge 402 can include an inlet 404. Solid sodium chloride and solid sodium acetate can be placed in a lower portion of the interior of salt cartridge 402. Water from water source 412 can be pumped through water line 413 and port 414 into sorbent recharger 401. As illustrated in FIG. 4, in certain embodiments the sorbent recharger 401 can use two pumps 432 and 433. Using two pumps allows fluid from multiple sources to be mixed in-line rather than using mixing chambers. However, one of skill in the art will understand that a single pump system can also be used. From inlet port 414, the water is pumped through fluid line 415 and T-junction 416 into fluid lines 417 and 418. The water is pumped through T-junction 419 and fluid line 420 to port 421. From port 421, the water can flow through fluid line 422 and into an empty upper portion of salt cartridge 402 through inlet 404. The water can soak filter pad 406 and the salt to generate the brine solution.

The water can dissolve at least a portion of the sodium acetate and sodium chloride in salt cartridge 402 and exit the salt cartridge 402 through outlet 405 into fluid line 409 and brine container 403. Filter pad 407 can be included between the sodium acetate and sodium chloride and outlet 405 of salt cartridge 402 to prevent solid material from entering fluid line 409. The brine solution can be recirculated through the flow path from brine container 403, through fluid line 410 and port 411 of the sorbent recharger 401 into fluid line 415, where the brine solution follows the same pathway as the water back into salt cartridge 402. During recirculation of the brine solution, acetic acid from acetic acid source 423 can be pumped through fluid line 424 and port 425 for addition to the brine solution recirculating in the flow path. Once the sodium acetate and sodium chloride are fully dissolved, the acetic acid is added, and a homogeneous brine solution is formed, the brine solution can be collected in brine container 403.

To recharge zirconium phosphate, a zirconium phosphate sorbent module can be placed in a receiving compartment (not shown) of the sorbent recharger 401. An inlet of the zirconium phosphate sorbent module can be connected to fluid line 415, and an outlet of the zirconium phosphate sorbent module can be fluidly connected to a drain or collection container (not shown). The control system can operate pump 432 and/or pump 433 to pump brine solution from brine container 403 through the zirconium phosphate sorbent module.

As described, in certain embodiments, the sorbent recharger 401 can include a receiving compartment for receiving a zirconium oxide sorbent module (not shown). To recharge zirconium oxide in a zirconium oxide sorbent module, bleach can be pumped from bleach container 429, through fluid line 430 to port 431. A separate flow path can direct the bleach solution through the zirconium oxide sorbent module to a drain or collection container. Sodium hydroxide from sodium hydroxide container 426 can be pumped through fluid line 427 and port 428, and then through the zirconium oxide sorbent module. Additional outlet ports can be included on the sorbent recharger 401, including outlet port 434, outlet port 435, and outlet port 436 for connection to waste collection containers, drains, or other components.

One of skill in the art will understand that FIG. 4 is a simplified diagram of a non-limiting embodiment of a sorbent recharger 401. Additional components, such as valves, sensors, additional pumps, and additional fluid lines can be included, as necessary. The control system can be programmed to control the pumps and valves to direct fluid through the proper flow paths for generating the brine solution and recharging the sorbent materials. As described, the salt cartridge 402 can be mounted on a base plate 408 to prevent the salt cartridge 402 from moving during use.

The described systems and methods allow for a "just in time" brine preparation. Rather than storing large quantities of premade brine solution, the salt cartridge system allows for preparation of the brine solution immediately before use. The time required to generate the brine solution using a salt cartridge can vary, but generally the generation of the brine solution will be under 1 hour, or about 45 minutes.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A system comprising:
 a sorbent recharger,
  the sorbent recharger comprising:
   i) a receiving compartment for a zirconium phosphate sorbent module;
   ii) at least a first fluid line fluidly connectable to an inlet of the zirconium phosphate sorbent module in the receiving compartment;
   iii) at least a second fluid line fluidly connectable to an outlet of the zirconium phosphate sorbent module; and
   iv) at least one pump;
 a brine container fluidly connectable to the first fluid line;
 a salt cartridge,
  wherein the salt cartridge comprises:
   an inlet fluidly connectable to a water source and an acetic acid source; and
   an outlet fluidly connectable to the brine container;
  wherein the salt cartridge contains sodium chloride and sodium acetate; and
 a control system,
  wherein the control system is programmed to:
   i) pump a preset volume of fluid from the water source through the salt cartridge;
   ii) recirculate fluid in a first flow path from the outlet of the salt cartridge to the brine container and then to the inlet of the salt cartridge; and
   iii) pump a preset volume of acetic acid into the first flow path.

2. The system of claim 1, wherein the inlet of the salt cartridge is on a top of the salt cartridge, and wherein the outlet of the salt cartridge is on a bottom of the salt cartridge.

3. The system of claim 1, further comprising a first filter pad in the salt cartridge between the inlet of the salt cartridge and the sodium chloride and sodium acetate.

4. The system of claim 1, further comprising a filter pad in the salt cartridge between the sodium chloride and sodium acetate and the outlet of the salt cartridge.

5. The system of claim 1, wherein the control system is further programmed to pump fluid from the brine container through the zirconium phosphate sorbent module.

6. The system of claim 1, wherein the control system is programmed to recirculate fluid in the first flow path until a homogeneous solution is generated in the first flow path.

7. The system of claim 1, wherein the salt cartridge further comprises a spring-loaded valve at the inlet.

8. The system of claim 1, wherein the salt cartridge further comprises a spring-loaded valve at the outlet.

9. The system of claim 1, wherein salt cartridge further comprises a solution diversion base; wherein the outlet of the salt cartridge is below the solution diversion base.

10. The system of claim 1, wherein the control system is programmed to recirculate fluid in the first flow path for a preset period of time.

11. The system of claim 1, wherein the sodium chloride and sodium acetate are initially solid.

12. A system comprising:
 a sorbent recharger,
  the sorbent recharger comprising:
   i) a receiving compartment for a zirconium phosphate sorbent module;
   ii) at least a first fluid line fluidly connectable to an inlet of the zirconium phosphate sorbent module in the receiving compartment;
   iii) at least a second fluid line fluidly connectable to an outlet of the zirconium phosphate sorbent module; and
   iv) at least one pump;
 a brine container fluidly connectable to the first fluid line;
 a salt cartridge,
  wherein the salt cartridge comprises:
   an inlet fluidly connectable to a water source and an acetic acid source; and
   an outlet fluidly connectable to the brine container,
    wherein the inlet is at a top of the salt cartridge and the outlet is at a bottom of the salt cartridge;
  wherein the salt cartridge contains sodium chloride and sodium acetate; and
 a control system,
  wherein the control system is programmed to:
   i) pump a preset volume of fluid from the water source through the salt cartridge;
   ii) recirculate fluid in a first flow path from the outlet of the salt cartridge to the brine container and then to the inlet of the salt cartridge; and
   iii) pump a preset volume of acetic acid into the first flow path.

13. The system of claim 12, further comprising a first filter pad in the salt cartridge between the inlet of the salt cartridge and the sodium chloride and sodium acetate.

* * * * *